(12) United States Patent
Brieden et al.

(10) Patent No.: US 8,258,338 B2
(45) Date of Patent: Sep. 4, 2012

(54) PROCESS FOR THE PREPARATION OF ENANTIOMERICALLY PURE 1-SUBSTITUTED-3-AMINOALCOHOLS

(75) Inventors: Walter Brieden, Ausserberg (CH); Martin Clausen, Brig (CH); John McGarrity, Brig-Glis (CH); Hanspeter Mettler, Visp (CH); Colette Mettler, legal representative, Visp (CH); Dominique Michel, Sierre (CH)

(73) Assignee: Lonza AG, Basel (CH)

( * ) Notice: Subject to any disclaimer, the term of this patent is extended or adjusted under 35 U.S.C. 154(b) by 907 days.

(21) Appl. No.: 11/884,542

(22) PCT Filed: Feb. 14, 2006

(86) PCT No.: PCT/EP2006/001334
§ 371 (c)(1),
(2), (4) Date: Nov. 10, 2008

(87) PCT Pub. No.: WO2006/087166
PCT Pub. Date: Aug. 24, 2006

(65) Prior Publication Data
US 2009/0156833 A1 Jun. 18, 2009

(30) Foreign Application Priority Data
Feb. 21, 2005 (EP) .................................. 05003657

(51) Int. Cl.
*C07C 33/32* (2006.01)
*C07D 333/12* (2006.01)
(52) U.S. Cl. .......................................... 562/114; 549/75
(58) Field of Classification Search .................... 549/75; 562/114
See application file for complete search history.

(56) References Cited

U.S. PATENT DOCUMENTS
4,948,813 A * 8/1990 Wilkerson ..................... 514/648
* cited by examiner Primary Examiner — Bernard Dentz
(74) Attorney, Agent, or Firm — Hoffman & Baron, LLP

(57) ABSTRACT

A process for the preparation of N-monosubstituted β-aminoalcohol sulfonates of formula (Ia), (Ib):

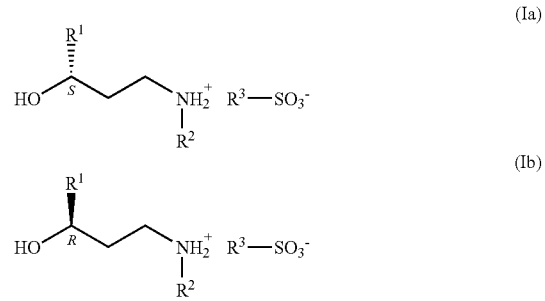

wherein $R^1$ is $C_{6-20}$-aryl or $C_{4-12}$-heteroaryl, each optionally being substituted with one or more halogen atoms and/or one or more $C_{1-4}$-alkyl or $C_{1-4}$-alkoxy groups, $R^2$ is $C_{1-4}$-alkyl or $C_{6-20}$-aryl, each aryl optionally being substituted with one or more halogen atoms and/or one or more $C_{1-4}$-alkyl or $C_{1-4}$-alkoxy groups and wherein $R^3$ is selected from the group consisting of $C_{1-18}$-alkyl, $C_{6-20}$-cycloalkyl, $C_{6-20}$-aryl and $C_{7-20}$-aralkyl residues. The process has the steps of (a) reacting a methyl ketone, a primary amine, formaldehyde and a sulfonic acid, at a pressure above 1.5 bar, optionally in a organic solvent, the organic solvent optionally containing water, to afford N-monosubstituted β-aminoketone sulfonates of formula (II):

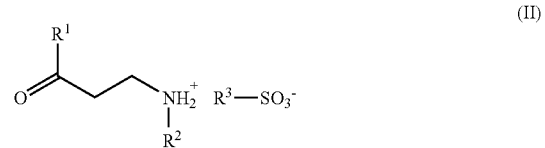

wherein $R^1$, $R^2$ and $R^3$ are as defined above, and (b) asymmetrically hydrogenating. The sulfonates in the presence of a base and a catalyst of a transition metal and a disphosphine ligand, in a polar solvent, optionally in the presence of water.

25 Claims, No Drawings

PROCESS FOR THE PREPARATION OF ENANTIOMERICALLY PURE 1-SUBSTITUTED-3-AMINOALCOHOLS

This subject application is a 371 national stage application of International Patent Application No. PCT/EP2006/001334, which was filed on Feb. 14, 2006, has priority benefit of U.S. Provisional Application No. 60/645,453, filed on Feb. 22, 2005, and has priority benefit of European Patent Application No. 05003657.3, filed on Feb. 21, 2005.

The invention relates to a process for the preparation of N-monosubstituted β-aminoalcohol sulfonates of formula

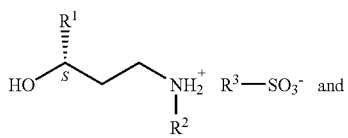

Ia and

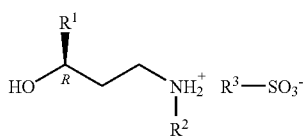

Ib wherein $R^1$ is $C_{6\text{-}20}$ aryl or $C_{4\text{-}12}$ heteroaryl, each optionally being substituted with one or more halogen atoms and/or one or more $C_{1\text{-}4}$ alkyl or $C_{1\text{-}4}$ alkoxy groups, $R^2$ is selected from the group consisting of $C_{1\text{-}4}$ alkyl, $C_{3\text{-}8}$ cycloalkyl and $C_{6\text{-}20}$ aryl, each aryl optionally being substituted with one or more halogen atoms and/or one or more $C_{1\text{-}4}$ alkyl or $C_{1\text{-}4}$ alkoxy groups, and wherein $R^3$ is selected from the group consisting of $C_{1\text{-}18}$ alkyl, $C_{6\text{-}20}$ cycloalkyl, $C_{6\text{-}20}$ aryl and $C_{7\text{-}20}$ aralkyl residues, comprising the steps of a) reacting a mixture comprising (i) a methyl ketone of formula

IV wherein $R^1$ is as defined above, (ii) a primary amine of formula

V, wherein $R^2$ is as defined above, and (iii) formaldehyde or a source of formaldehyde selected from the group consisting of formaldehyde in aqueous solution, 1,3,5-trioxane, paraformaldehyde and mixtures thereof, in the presence of a sulfonic acid of the formula

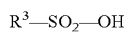

VI wherein $R^3$ is as defined above, optionally in an organic solvent, said organic solvent optionally containing water, to afford a β-aminoketone sulfonate of formula

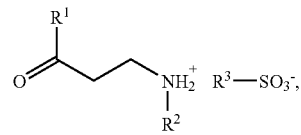

II wherein $R^1$, $R^2$ and $R^3$ are as defined above, and b) asymmetrically hydrogenating said sulfonate, to afford a β-aminoalcohol sulfonate of formula I, wherein $R^1$, $R^2$ and $R^3$ are as defined above, in the presence of a base and a catalyst, the catalyst comprising a transition metal and a diphosphine ligand, at a hydrogen pressure of 5 to 50 bar, in a polar solvent, optionally in the presence of water.

(S)-(−)-3-N-Methylamino-1-(2-thienyl)-1-propanol is an intermediate for the preparation of (S)-(+)-methyl-[3-(1-naphthyloxy)-3-(2-thienyl)-propyl]-amine (duloxetine), an agent for the treatment of depression and urinary incontinence (Huiling et al. *Chirality* 2000, 12, 26-29, Sorbera et al. *Drugs of the Future* 2000, 25(9), 907-916).

The reaction of step a) in the presence of an inorganic or carboxylic acid has been disclosed in WO-A 2004/005239 and affords the salts of said inorganic or carboxylic salts of the compounds of formula II. This process has the disadvantage of a long reaction time of about 8 h or more in an autoclave vessel. Pressurized reactions bear the risk of damages, which increases with the reaction time.

N-Monosubstituted β-aminoketones were first synthesized in 1922 by reacting methyl ketones with formaldehyde and primary or secondary alkylamines in the presence of hydrochloric acid (Mannich, C. et al., *Chem. Ber.* 1922, 55, 356-365). In said reactions with primary alkylamines formation of tertiary β-keto amino hydrochlorides of formula

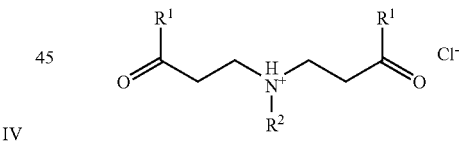

prevails over formation of secondary β-keto amino hydrochlorides. These findings were supported by Blicke et al. (*J. Am. Chem. Soc.* 1942, 64, 451-454) and Becker et al. (*Wiss. Z. Tech. Hochsch. Chem. Leuna-Merseburg.* 1969, 11, 38-41).

According to Mannich et al., steam distillation of tertiary β-aminoketones results in formation of secondary β-aminoketones in fairly satisfactory yields, accompanied by vinyl compounds and other by-products. Poor yields of tertiary β-keto amines of about 40 to 60% and loss of more than 50% at subsequent cleavage render the Mannich method unsuitable for industrial production. After steam distillation of the β-aminoketone hydrochloride of formula III, wherein $R^1$ is thienyl and $R^2$ is methyl, there is no evidence of formation of the corresponding secondary N-monomethyl β-aminoketone (Blicke et al.).

Several methods for racemic and asymmetric hydrogenation of thienyl aminoketones are known, as well as processes for chiral resolution of 3-N-methylamino-1-(2-thienyl)-1- propanol (WO-A 2003/062219, FR-A 2841899, WO-A 2004/005220, WO-A 2004/005307).

Huiling et al. describe a preparation of (S)-(−)-3-N-methylamino-1-(2-thienyl)-1-propanol from thiophene. Thiophene is converted with 3-chloropropanoyl chloride in the presence of tin tetra-chloride in benzene to 3-chloro-1-(2-thienyl)-1-propanone, which is reduced with sodium boro-hydride in ethanol to 3-chloro-1-(2-thienyl)-1-propanol. Kinetic resolution by transesterification using vinyl butanoate and lipase B from *Candida antarctica* as catalyst in hexane yielded (S)-3-chloro-1-(2-thienyl)-1-propanol, which is converted to (S)-3-iodo-1-(2-thienyl)-1-propanol using sodium iodide in acetone. Subsequent treatment with methylamine in tetrahydrofuran afforded (S)-(−)-3-N-methylamino-1-(2-thienyl)-1-propanol.

Sorbera et al. disclose another preparation of (S)-(−)-3-N-methylamino-1-(2-thienyl)-1-propanol from thiophene, which is essentially the same as the one known from Huiling et al. except that 3-chloro-1-(2-thienyl)-1-propanone is asymmetrically reduced to (S)-3-chloro-1-(2-thienyl)-1-propanol using borane and catalytic amounts of (R)-3,3-diphenyl-1-methyltetrahydro-3H-pyrrolo[1,2-c][1,3,2]oxazaborole in THF. This asymmetric reduction afforded (s)-3-chloro-1-(2-thienyl)-1-propanol in a yield of 86% from 3-chloro-1-(2-thienyl)-1-propanone (Wheeler et al. *J. Label. Compd. Radiopharm.* 1995, 36, 213-223).

In Sakuraba et al., *Chem. Pharm. Bull.* 1995, 43, 748-753 and JP-A 50-70412, asymmetric hydrogenation of HCl salts of 3-N-methylamino-1-phenyl-1-propanol and 3-amino-1-phenyl-1-propanone is disclosed. EP-A 457559 discloses the preparation of HCl salts of 3-dimethyl-amino-1-(2-thienyl)-1-propanone and (S)-(−)-N,N-dimethyl-3-(2-thienyl)-3-hydroxypropan-amine as well as the oxalate salts of (S)-(+)-N,N-dimethyl-3-(1-napthalenyloxy)-3-(2-thienyl)-propanamine and (S)-(−)-N,N-dimethyl-3-(1-naphthalenyloxy)-3-(2-thienyl)propanamine.

Although several processes for asymmetric hydrogenation of the aminoketones of formula-II are known, most stringent requirements of national registration authorities regarding optical purity of chiral pharmaceutically active compounds necessitate constantly improving the preparation processes.

The drawbacks of the above processes for the preparation of (S)-(−)-3-N-methylamino-1-(2-thienyl)-1-propanol, are the use of toxic or carcinogenic compounds such as tin tetrachloride and benzene and/or the use of expensive compounds such as borane or sodium iodide, the latter being in addition difficult to dispose of. The disclosed asymmetric hydrogenation processes with diphosphines are not satisfying in regard of the hydrogenation of 3-N-methylamino-1-(2-thienyl)-1-propanone.

It is an object of the present invention to provide an economically and ecologically improved process for the preparation of enantiomerically pure N-monosubstituted-3-aminoalcohols, particularly of (S)-(−)- and (R)-(+)-3-N-methylamino-1-(2-thienyl)-1-propanol. Furthermore, the present invention provides an improved process for the preparation of the aminoketones of formula II, which makes the sulfonates thereof directly accessible.

These objects are achieved by the process of claim 1.

Provided is a process for the preparation of N-monosubstituted β-aminoalcohol sulfonates of formula

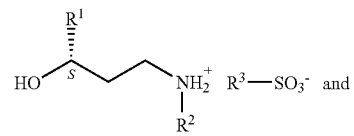

Ia

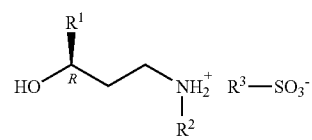

Ib wherein $R^1$ is $C_{6-20}$ aryl or $C_{4-12}$ heteroaryl, each optionally being substituted with one or more halogen atoms and/or one or more $C_{1-4}$ alkyl or $C_{1-4}$ alkoxy groups, $R^2$ is selected from the group consisting of $C_{1-4}$ alkyl $C_{3-8}$ cycloalkyl and $C_{6-20}$ aryl, each aryl optionally being substituted with one or more halogen atoms and/or one or more $C_{1-4}$ alkyl or $C_{1-4}$ alkoxy groups, and wherein $R^3$ is selected from the group consisting of $C_{1-18}$ alkyl, $C_{6-20}$ cycloalkyl, $C_{6-20}$ aryl and $C_{7-20}$ aralkyl residues, comprising the steps of a) reacting a mixture comprising
   (i) a methyl ketone of formula

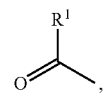

IV wherein $R^1$ is as defined above,
   (ii) a primary amine of formula $$H_2N-R^2$$ V, wherein $R^2$ is as defined above,
   (iii) formaldehyde or a source of formaldehyde selected from the group consisting of formaldehyde in aqueous solution, 1,3,5-trioxane, paraformaldehyde and mixtures thereof, in the presence of a sulfonic acid of the formula $$R^3-SO_2-OH$$ VI wherein $R^3$ is as defined above,
optionally in an organic solvent, said organic solvent optionally containing water, to afford a β-aminoketone sulfonate of formula

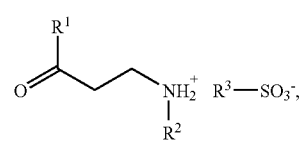

II wherein $R^1$, $R^2$ and $R^3$ are as defined above,
and
b) asymmetrically hydrogenating said sulfonate, to afford a β-aminoalcohol sulfonate of formula I, wherein $R^1$, $R^2$ and $R^3$ are as defined above, in the presence of a base and a catalyst, the catalyst comprising a transition metal and a diphosphine ligand, at a hydrogen pressure of 5 to 50 bar, in a polar solvent, optionally in the presence of water.

The term "enantiomerically pure compound" comprises optically active compounds with an enantiomeric excess (ee) of at least 85%.

The term "$C_{1-n}$ alkyl", for example "$C_{1-18}$ alkyl", represents a linear or branched alkyl group having 1 to n carbon atoms. Optionally with one or more halogen atoms substituted $C_{1-18}$ alkyl represents for example methyl, ethyl, propyl, isopropyl, butyl, isobutyl, sec-butyl, tert-butyl, pentyl, hexyl, octyl, decyl, dodecyl and octadecyl.

The term "$C_{1-n}$ alkoxy", for example "$C_{1-6}$ alkoxy", represents a linear or branched alkoxy group having 1 to n carbon atoms. Optionally with one or more halogen atoms substituted $C_{1-6}$ alkoxy represents for example methoxy, ethoxy, propoxy, isopropoxy, butoxy, isobutoxy, sec-butoxy, tert-butoxy, pentyloxy and hexyloxy.

The term "$C_{3-n}$ cycloalkyl", for example "$C_{3-10}$ cycloalkyl", represents a cycloaliphatic group having 3 to n carbon atoms. Optionally with one or more halogen atoms substituted $C_{3-10}$ cycloalkyl represents for example mono- and polycyclic ring systems such as cyclopropyl, cyclobutyl, cyclopentyl, cyclohexyl, cycloheptyl, cyclooctyl, adamantyl or norbornyl.

The term "$C_{6-n}$ aryl", for example $C_{6-20}$ aryl, represents an aromatic group having 6 to n carbon atoms, optionally being substituted with one or more halogen atoms, amino groups, and/or optionally substituted $C_{1-6}$ alkyl, $C_{1-6}$ alkoxy or di-$C_{1-6}$-alkylamino groups, wherein the alkyl moieties optionally are substituted with one or more halogen atoms. $C_{6-20}$ Aryl represents for example phenyl or naphthyl and derivatives thereof as outlined above.

The term "$C_{4-n}$ heteroaryl", for example $C_{4-12}$ heteroaryl, represents an heteroaromatic group having 4 to n carbon atoms and containing 1 to 2 heteroatoms independently selected from the group consisting of nitrogen, oxygen or sulfur, optionally being substituted with one or more halogen atoms, amino groups, and/or optionally substituted $C_{1-6}$ alkyl, $C_{1-6}$ alkoxy or di-$C_{1-6}$-alkylamino groups, wherein the alkyl moieties optionally are substituted with one or more halogen atoms. $C_{4-12}$ Heteroalkyl represents for example furyl or thienyl and derivatives thereof as outlined above, preferably 2-furyl and 2-thienyl.

The term "$C_{7-n}$ aralkyl", for example $C_{7-20}$ aralkyl, represents an aromatic group having 7 to n carbon atoms, wherein the alkyl moiety of the aralkyl residue is linear $C_{1-8}$ alkyl and the aryl moiety is selected from the group consisting of phenyl, naphthyl, furanyl, thienyl, benzo[b]furanyl, benzo[b]thienyl, optionally being substituted with one or more halogen atoms, amino groups, and/or optionally substituted $C_{1-6}$ alkyl, $C_{1-6}$ alkoxy or di-$C_{1-6}$-alkylamino groups. $C_{6-20}$ Aryl represents for example benzyl or phenylethyl and derivatives thereof as outlined above.

Furthermore, it is provided a process for the preparation of N-monosubstituted β-aminoalcohol sulfonates of formula

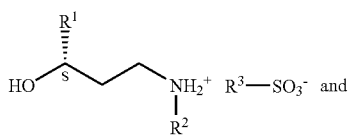

Ia

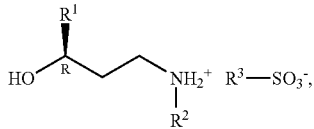

Ib wherein $R^1$ is $C_{6-20}$ aryl or $C_{4-12}$ heteroaryl, each optionally being substituted with one or more halogen atoms and/or one or more $C_{1-4}$ alkyl or $C_{1-4}$ alkoxy groups, $R^2$ is selected from the group consisting of $C_{1-4}$ alkyl, $C_{3-8}$ cycloalkyl and $C_{6-20}$-aryl, each aryl optionally being substituted with one or more halogen atoms and/or one or more $C_{1-4}$ alkyl or $C_{1-4}$ alkoxy groups, and $R^3$ is selected from the group consisting of $C_{1-18}$ alkyl, $C_{6-20}$ cycloalkyl, $C_{6-20}$ aryl and $C_{7-20}$ aralkyl residues, comprising asymmetrically hydrogenating β-aminoketone sulfonates of formula

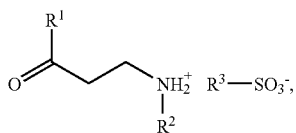

II wherein $R^1$, $R^2$ and $R^3$ are as defined above, in the presence of a base and a catalyst, the catalyst comprising a transition metal and a diphosphine ligand, at a hydrogen pressure of 5 to 50 bar, in a polar solvent, optionally in the presence of water.

In a preferred embodiment in the processes comprising steps a) and b) or step b) only, $R^1$ is selected from the group consisting of phenyl, 1-naphthyl, 2-furanyl, and 2-thienyl, each being optionally being substituted with halogen, linear or branched $C_{1-4}$ alkyl, linear or branched $C_{1-4}$ alkoxy, $C_{3-8}$ cycloalkyl, $CF_3$, $C_2F_5$, $OCF_3$ or $OC_2F_5$.

In a further preferred embodiment $R^2$ represents a residue selected from the group consisting of linear or branched $C_{1-4}$ alkyl, $C_{3-8}$ cycloalkyl, phenyl, 1-naphthyl, benzyl and ethylbenzyl, each aryl or aralkyl optionally being substituted with halogen, linear or branched $C_{1-4}$ alkyl, linear or branched $C_{1-4}$ alkoxy, $C_{3-6}$ cycloalkyl, $CF_3$, $C_2F_5$, $OCF_3$ or $OC_2F_5$. Particularly preferred the methyl ketone of formula IV of step a) is 2-furyl methyl ketone (2-acetylfuran), methyl 2-thienyl ketone (acetylthiophene) or methyl phenyl ketone (acetophenone).

The primary amine may be used as free base of formula IV, as defined above or as a corresponding sulfonate.

It is also particularly preferred that the primary amine of formula V in step a) is a linear or branched $C_{1-4}$ alkyl amine, more particularly preferred is methyl amine, ethyl amine, propyl amine, isopropyl amine, butyl amine, isobutyl amine or tert-butyl amine, each as free base or as a corresponding sulfonate.

In a preferred embodiment the primary amine of formula V in step a) is present in an amount at least equimolar to that of the methyl ketone of formula IV. Particularly preferred the molar ratio of the methyl ketone of formula IV to the primary amine of formula IV is between 1:1 and 1:2.

Particularly preferred are processes comprising steps a) and b) or step b) only, wherein $R^1$ is 2-thienyl or phenyl, each optionally being substituted with one or more halogen atoms and $R^2$ is selected from the group consisting of methyl, ethyl, tert-butyl and cyclopropyl.

Even more preferred in the processes comprising steps a) and b) or step b) only, wherein the compound of formula I is selected from the group consisting of (S)-(−)-3-N-methylamino-1-(2-thienyl)-1-propanol, (S)-(−)-3-N-methylamino-1-(3-chloro-2-thienyl)-1-propanol, (R)-(+)-3-N-methylamino-1-(2-thienyl)-1-propanol and (R)-(+)-3-N-methylamino-1-(3-chloro-2-thienyl)-1-propanol.

Using sulfonic acids instead of inorganic or carboxylic acids disclosed in WO-A 2004/005239 reduces the required reaction times under pressure of step a) dramatically from about 8 h to about 1 to 4 h. In addition, when using sulfonic acids corrosion issues can be neglected compared to most inorganic acids. Additionally, sulfonic acids are usually liquids or solids with low vapour pressure and odor and are therefore easy to handle. Moreover, sulfonates tend to crystallize easily and thus facilitate recovery of the products of steps a) and/or b) of the inventive process. A large variety of sulfonic acids is available, since these compounds are of immense technical interest as lubricants, softeners, emulsifying agents and surfactants for example for washing, oil drilling and yarn spinning purposes.

In a preferred embodiment in the processes comprising steps a) and b) or step b) only, $R^3$ of the sulfonic acid of the formula VI is selected from the group consisting of
i) linear or branched alkyl residues, consisting of 1 to 18 carbon atoms, containing one or more substituents of the group consisting of amino, halogen and hydroxy,
ii) mono- or polycyclic cycloalkyl residues, consisting of 6 to 20 carbon atoms, optionally containing one or more nitrogen or oxygen atoms and/or one or more substituents of the group consisting of amino, halogen, hydroxy and oxygen, and
iii) mono- or polycyclic aryl or aralkyl residues, consisting of 6 to 20 carbon atoms, optionally containing one or more nitrogen or oxygen atoms and/or one or more substituents of the group consisting of amino, halogen and hydroxy.

Without limitation, according to i) above, $R^3$ of the sulfonic acids of formula VI can be methyl, ethyl, isopropyl, butyl, sec-butyl, tert-butyl, perfluoro-$C_{1-6}$-alkyl, trifluoromethyl, trichloro-methyl, perfluoroethyl, perchloroethyl, hydroxymethyl, 2-hydroxyethyl and 2-aminoethyl.

Without limitation, according to ii) above, an example for a polycycloaliphatic sulfonic acid of formula IV having an oxygen substituent attached to the ring is 7,7-dimethyl-2-oxobi-cyclo[2.2.1]hept-1-yl)methanesulfonic acid.

Further non-limiting examples of sulfonic acids, containing mono-, polycyclic cycloalkyl, mono- or polycyclic aryl or aralkyl residues are cumenesulfonic acid, guaiacolsulfonic acid, morpholinopropanesulfonic acids, hydroxy-(2-hydroxy-phenyl)-methanesulfonic acid, benzene-sulfonic acid, 3,5-dihydroxybenzenesulfonic acid, 2-, 3-, or 4-aminobenzenesulfonic acid, diaminobenzenesulfonic acid, 4-(N-methylanilino)-benzenesulfonic acid, 2-, 3-, or 4-chloro-benzenesulfonic acid, 2-, 3-, or 4-hydroxybenzenesulfonic acid, 2,5-dihydroxybenzenesulfonic acid, 4-dodecyl-benzenesulfonic acid, dodecyl-, 4-hydroxybenzenesulfonic acid, 2-, 3- or 4-toluenesulfonic acid, anthraquinone-1-sulfonic acid, anthraquinone-2-sulfonic acid, anthra-quinone-2,7-disulfonic acid, naphthalene-2-sulfonic acid, 4-amino-naphthalenesulfonic acid, 3-chloro-2-naphthalenesulfonic acid, 5-hydroxy-1-naphthalenesulfonic acid, naphthalene-1,4-disulfonic acid, naphthalene-1,5-disulfonic acid, naphthalene-2,6-disulfonic acid, 8-amino-naphthalene-1-sulfonic acid, 5-aminonaphthalene-2-sulfonic acid, 4-aminonaphthalene-1-sulfonic acid, 2-aminonaphthalene-1-sulfonic acid, 8-aminonaphthalene-2-sulfonic acid, 5-aminonaphthalene-1-sulfonic acid, 4-amino-3-hydroxynaphthalene-2-sulfonic acid, 6-amino-4-hydroxynaphthalenesulfonic acid, 5-dimethylaminonaphthalene-1-sulfonic acid, 5-hydroxy-naphthalene-1-sulfonic acid, 7-hydroxynaphthalene-2-sulfonic acid, 6-hydroxynaphthalene-2-sulfonic acid, 4-hydroxynaphthalene-1-sulfonic acid, 3-hydroxy-4-(2-imidazolylazo)-1-sulfonic acid, 6-hydroxy-5-(2-pyridylazo)-naphthalene-2-sulfonic acid, 6-hydroxynaphthalene-2-sulfonic acid, isatin-5-sulfonic acid and ligninsulfonic acids.

Particularly preferred the sulfonic acid is selected from the group consisting of methanesulfonic acid, ethanesulfonic acid, (7,7-dimethyl-2-oxobicyclo[2.2.1]hept-1-yl)methanesulfonic acid, p-toluenesulfonic acid and benzenesulfonic acid.

In a further preferred embodiment the organic solvent in step a) is inert towards the reaction conditions in steps a). More preferred the organic solvent comprises alcohols, carboxylic esters, ethers, thioethers, sulfones, sulfoxides and mixtures thereof, optionally containing further additives, cosolvents or water. In a preferred embodiment alcohols are linear or branched $C_{1-12}$ alkyl alcohols.

Particularly preferred aliphatic alcohols are linear or branched aliphatic or cycloaliphatic $C_{1-12}$ alcohols, including di- and/or trimeric ethylene glycols or mono $C_{1-4}$ alkyl or acetyl derivatives thereof, each of said $C_{1-12}$ alcohols containing 1 to 3 hydroxy groups.

Examples for suitable $C_{1-12}$ alcohols are methanol, ethanol, propanol, isopropyl alcohol, butanol, isobutanol, tert-butanol, 2-butanol, 1-pentanol, 2-pentanol, 3-pentanol, 1-hexanol, 2-hexanol, 2,2,2-trifluorethanol, 1,2-ethanediol, 1,2-propanediol, 1,2-butanediol, 2,3-butane-diol, 1,4-butanediol, 1,2,3-propanetriol, 1,2,6-hexanetriol, diethylene glycol, diethylene glycol monomethyl ether, diethylene glycol monoethyl ether, diethylene glycol monobutyl ether, diethylene glycol monoacetate, triethylene glycol, triethylene glycol monomethyl ether, tri-ethylene glycol monoethyl ether, triethylene glycol monobutyl ether or triethylene glycol monoacetate.

Particularly preferred alcohols can be selected from the group consisting of ethanol, propanol, isopropyl alcohol, butanol, isobutanol, tert-butanol, diethylene glycol and triethylene glycol.

Carboxylic esters suitable in the reaction of step a) are for example ethylacetate or butylacetate.

In a preferred embodiment ethers and thioethers are dialkyl or alkylaryl ethers or thioethers, the linear or branched alkyl moieties being independently $C_{1-6}$ alkyl, the aryl moieties being phenyl.

In a further preferred embodiment ethers and thioethers are $C_{3-8}$ cycloalkyl ethers and $C_{3-8}$ cycloalkyl thioethers, containing 1 to 2 oxygen or sulfur atoms.

Particularly preferred ethers, thioethers, sulfones and sulfoxides can be selected from the group consisting of dimethyl ether, diethyl ether, ethyl methyl ether and tert-butyl methyl ether, tetrahydrofuran, 1,4-dioxane, dimethyl sulfide, diethyl sulfide, ethyl methyl sulfide and tert-butyl methyl sulfide, 1,4-dithiane, thiolane, sulfolane and dimethylsulfoxide.

In a preferred embodiment the pressure during reaction step a) is above 1.5 bar, more preferably in the range of 1.5 to 10 bar and particularly preferred in the range of 1.5 to 5 bar.

In a further preferred embodiment the reaction of step a) is carried out at a temperature of 80 to 150° C., preferably of 100 to 130° C.

The preferences mentioned in step a) above regarding the residues $R^1$, $R^2$ and $R^3$ in the compounds of formulae I, II and VI also apply in step b) in the following part.

Although we found the salts of sulfonic acids of the β-aminoketones of formula II much easier to handle compared to the respective inorganic or organic salts, asymmetrically hydrogenating of said sulfonates gave only poor yields using known methods with transition metals and diphosphine ligands.

Surprisingly, in the presence of a base during hydrogenating yields were increased dramatically and even the enantiomeric excess (ee) of the β-aminoalcohols has been improved. Additionally, in several examples the substrate/catalyst ratio (S/C) has also been raised remarkably (table 4). Another surprising effect of the added base is the possibility to reduce the temperature during hydrogenating from about 50 to 80° C. to 25 to 50° C. This improves the stability of the chiral products and the starting materials. We found no difference whether the β-aminoketone has been added as a sulfonate or as the corresponding free base and a sulfonic acid.

In a preferred embodiment of step b), the base is present in a ratio of 0.05 to 0.5 molar equivalents (0.05 to 0.5 eq) regarding to the β-aminoketone of formula II.

Particularly preferred, the base is an inorganic base. Even more preferred the inorganic base is a metal carbonate. More particularly preferred the metal carbonate is an alkaline or earth alkali carbonate. In a preferred embodiment, the base is selected from the group consisting of $Li_2CO_3$, $Na_2CO_3$ and $K_2CO_3$.

The catalyst used in step b) comprises at least a transition metal and a diphosphine ligand.

In a preferred embodiment, the transition metal is selected from the group consisting of rhodium, ruthenium and iridium, preferably rhodium.

In another further preferred embodiment, the diphosphine ligand is selected from the group consisting of

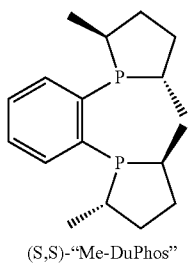

(S,S)-"Me-DuPhos"

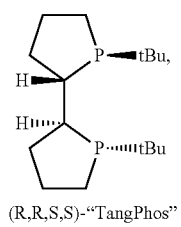

(R,R,S,S)-"TangPhos"

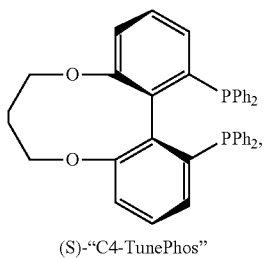

(S)-"C4-TunePhos"

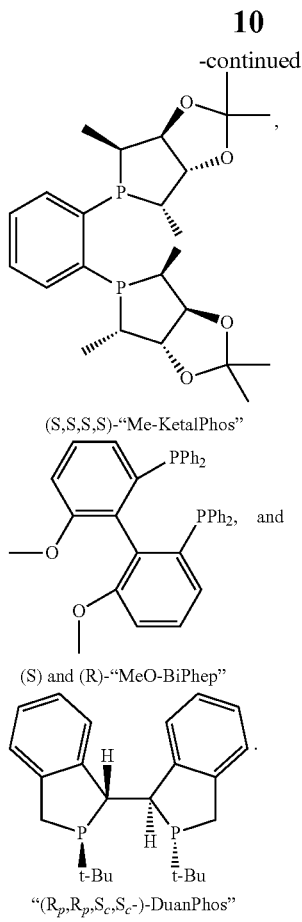

(S,S,S,S)-"Me-KetalPhos"

(S) and (R)-"MeO-BiPhep"

"($R_p,R_p,S_c,S_c$-)-DuanPhos"

The catalyst solution can be prepared in situ by dissolving a ruthenium salt $Ru^{n+}Y^-_n$, wherein n is 2 or 3 and wherein $Y^-$ is $Cl^-$, $Br^-$, $I^-$, $BF_4^-$, $AsF_6^-$, $SbF_6^-$, $PF_6^-$, $ClO_4^-$ or $OTf^-$ (trifluormethane sulfonate or triflate) or another suitable counterion in a polar solvent and mixing with a suitable amount of the diphosphine ligands, optionally further mixed with at least one stabilizing ligand.

Alternatively, the catalyst solution can be obtained by mixing a catalyst precursor complex, i.e. a preformed ruthenium complex which already contains at least one stabilizing ligand, in a polar solvent with a suitable amount of further diphosphine ligands. The catalyst precursor complex comprises at least one stabilizing ligand such as a diene, alkene or arene. In a preferred embodiment the stabilizing ligand is 1,5-cyclooctadiene (cod), norbornadiene (nbd) or p-cymene (cym). Particularly preferred the stabilizing ligand is p-cymene.

In a further preferred embodiment the catalyst precursor complex comprises at least one chiral diphosphine ligand.

In a further particularly preferred embodiment the catalyst precursor complex comprises at least one polar solvent molecule as stabilizing ligand, such as dimethylsulfoxide (DMSO), dimethyl-formamide (DMF) or acetonitrile (MeCN).

Examples for catalyst precursor complexes containing such stabilizing ligands are [$Rh_2Cl_4(cym)_2$], [$Rh_2Br_4(cym)_2$], [$RhCl((R_P,R_P,S_C,S_C)$-DuanPhos)(benzene)]Cl, [$RhCl_2((R_P,R_P,S_C,S_C)$-DuanPhos).DMF], [$RhCl_2((R_P,R_P,S_C,S_C)$-DuanPhos).DMSO] and [$Rh_2Cl_4(cod)_2.MeCN$].

Furthermore, the catalyst solution can be obtained by dissolving a preformed chiral ruthenium complex which already contains all required diphosphine ligands.

Several examples for general applicable methods for the preparations of catalysts and catalyst solutions are disclosed in Ashworth, T. V. et al. *S. Afr. J. Chem.* 1987, 40, 183-188, WO 00/29370 and Mashima, K. *J. Org. Chem.* 1994, 59, 3064-3076.

In a particularly preferred embodiment the catalyst composition corresponds to an idealized formula selected from the group consisting of [Rh((R,R,S,S)-Tangphos)(norbornadiene)]BF$_4$, [(S,S)-Me-Duphos-Rh]BF$_4$ and [Rh(NBD)(R$_P$, R$_P$,S$_C$,S$_C$-DuanPhos)]BF$_4$.

In yet another preferred embodiment the catalyst comprises the diphosphine ligand "(R$_P$,R$_P$,S$_C$,S$_C$)-DuanPhos", optionally containing further components as outlined above.

In a preferred embodiment the pressure during hydrogenation in step b) is above 1.5 bar, more preferably in the range of 1.5 to 50 bar and particularly preferred in the range of 5 to 40 bar.

In a further preferred embodiment the reaction of step b) is carried out at a temperature of 0 to 80° C., preferably of 20 to 50° C.

The hydrogenation is carried out with a catalyst solution in a polar solvent selected from the group consisting of C$_{1-4}$-alcohols, ethers, thioethers, dimethylsulfoxide (DMSO), dimethylformamide (DMF), acetonitrile (MeCN) or mixtures thereof and is inert towards hydrogenation in the presence of the catalyst.

In a preferred embodiment ethers and thioethers are dialkyl or alkylaryl ethers or thioethers, the linear or branched alkyl moieties being independently C$_{1-6}$ alkyl, the aryl moieties being phenyl. In a further preferred embodiment ethers and thioethers are C$_{3-8}$ cycloalkyl ethers and C$_{3-8}$ cycloalkyl thioethers.

Particularly preferred ethers and thioethers can be selected from the group consisting of dimethyl ether, diethyl ether, ethyl methyl ether and tert-butyl methyl ether, tetrahydrofuran, dimethyl thioether, diethyl thioether, ethyl methyl thioether and tert-butyl methyl thioether, thiolane and sulfolane.

Preferably the polar solvent is selected from the group consisting of methanol, ethanol, isopropyl alcohol, dimethyl ether, tetrahydrofuran, ethylacetate and a mixture thereof.

In any case the solvent used in step b) may contain further solvent additives like dichloro-methane.

In a further preferred process, the free bases of the compounds of formulae Ia and Ib are obtainable from the corresponding salts by aqueous hydrolysis in the presence of a base, preferably an alkali or earth alkali hydroxide, like NaOH, KOH, Ca(OH)$_2$ or Mg(OH)$_2$.

The present invention also provides β-aminoketone sulfonates of formula

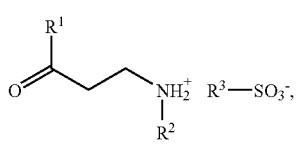

II wherein R$^1$ represents C$_{6-20}$ aryl or C$_{4-12}$ heteroaryl, each optionally being substituted with one or more halogen and/or one or more C$_{1-4}$ alkyl or C$_{1-4}$ alkoxy groups, R$^2$ is selected from the group consisting of linear or branched C$_{1-4}$ alkyl, C$_{3-8}$ cycloalkyl and C$_{6-20}$ aryl, the aryl moiety optionally being substituted with one or more halogen atoms and/or one or more C$_{1-4}$ alkyl or C$_{3-6}$ cycloalkyl, and wherein R$^3$ is selected from the group consisting of C$_{1-18}$ alkyl, C$_{6-20}$ cycloalkyl, C$_{6-20}$ aryl and C$_{7-20}$ aralkyl residues, and a sulfonic acid of formula

VI wherein R$^3$ is as defined above.

The present invention also provides β-aminoketone sulfonates of formula

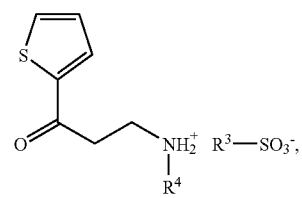

VII wherein R$^3$ is as defined above and R$^4$ represents methyl, ethyl, isobutyl and tert-butyl.

The present invention also provides β-aminoketone sulfonates of formula

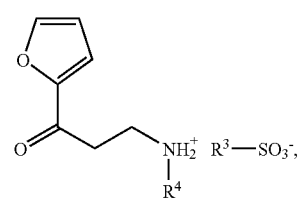

VIII wherein R$^3$ is as defined above and R$^4$ represents methyl, ethyl, isobutyl and tert-butyl.

Furthermore, the present invention also provides β-aminoketone sulfonates of formula

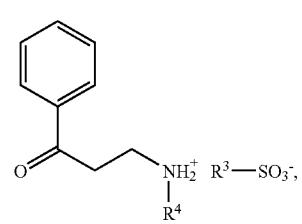

IX wherein R$^3$ is as defined above and R$^4$ represents methyl, ethyl, isobutyl and tert-butyl.

The present invention also provides β-aminoketone sulfonates of formula

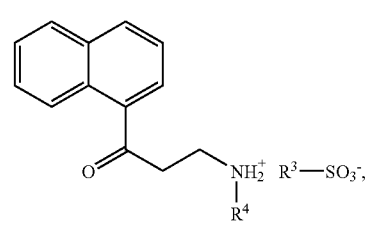

X wherein R³ is as defined above and R⁴ represents methyl, ethyl, isobutyl and tert-butyl.

The present invention provides β-aminoalcohol sulfonates of formula

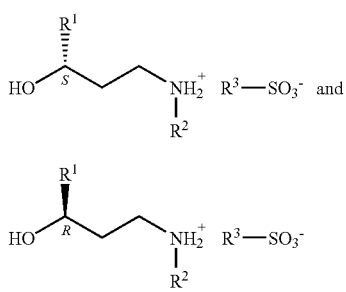

Ia

Ib wherein R¹ is $C_{6-20}$ aryl or $C_{4-12}$ heteroalkyl, each optionally being substituted with one or more halogen atoms and/or one or more $C_{1-4}$ alkyl or $C_{1-4}$ alkoxy groups, R² is $C_{1-4}$ alkyl or $C_{6-20}$ aryl, wherein the aryl moiety optionally being substituted with one or more halogen atoms and/or $C_{1-4}$ alkyl or $C_{1-4}$ alkoxy groups, and wherein R³ is selected from the group consisting of $C_{1-18}$ alkyl, $C_{6-20}$ cycloalkyl, $C_{6-20}$ aryl and $C_{7-20}$ aralkyl residues, and
a sulfonic acid of formula

V, wherein R³ is as defined above.

The present invention also provides β-aminoalcohol sulfonates of formula

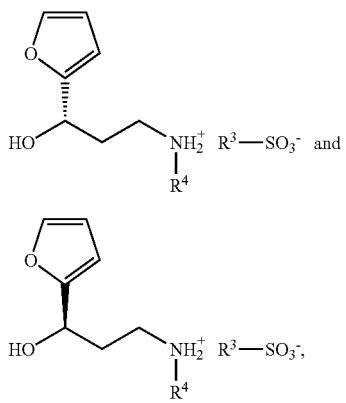

XIa

XIb wherein R³ is as defined above and R⁴ represents methyl, ethyl, isobutyl and tert-butyl.

The present invention also provides β-aminoalcohol sulfonates of formula

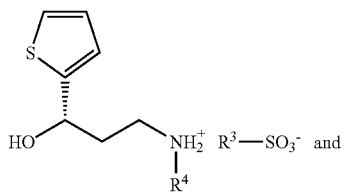

XIIa

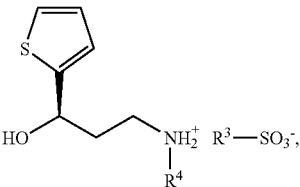

XIIb wherein R³ is as defined above and R⁴ represents methyl, ethyl, isobutyl and tert-butyl.

The present invention also provides β-aminoalcohol sulfonates of formula

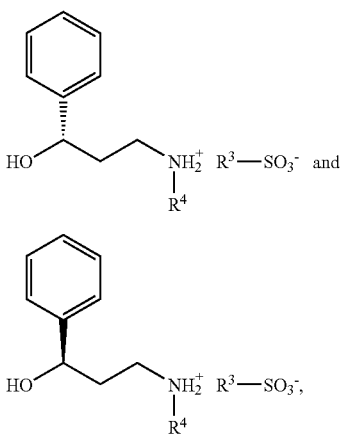

XIIIa

XIIIb wherein R³ is as defined above and R⁴ represents methyl, ethyl, isobutyl and tert-butyl.

The present invention also provides β-aminoalcohol sulfonates of formula

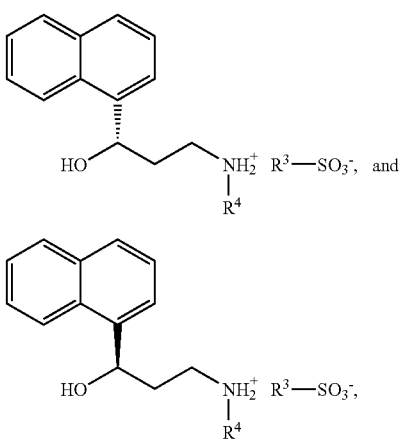

XIVa

XIVb wherein R³ is as defined above and R⁴ represents methyl, ethyl, isobutyl and tert-butyl.

The present invention is illustrated by the following non-limiting examples.

Steps a) and b) of the present process are outlined in examples 1 to 17 and 21 to 26 no respectively. Since β-aminoketone sulfonates of formula II in principle are obtainable by acid exchange, for example of the respective hydrochlorides as outlined in examples 18 to 20, the present invention also provides a process, comprising only step b) starting of β-aminoketone sulfonates of formula II. Examples 27 and 28 are directed to prepare β-aminoalcohol sulfonates of formula I via acid exchange starting from the corresponding hydrochlorides. Thus the present invention provides a feasible method for acid exchange.

EXAMPLE 1

A mixture of ethanol (40 mL), methylammonium methanesulfonate (MAMS) (16.5 g, 130 mmol), 2-acetylthiophene (11.0 g, 87.2 mmol) and paraformaldehyde (2.6 g, 86.6 mmol) in an autoclave is heated to 120° C. at a total pressure of 4.5 bar. After 3 h at that temperature, the autoclave is cooled to 25° C. The reaction mixture is concentrated to dryness and a mixture of ethanol (20 mL) and ethyl acetate (400 mL) is added to the residue, then the resulting suspension is stirred for 30 minutes at 25° C. Afterwards, the precipitate is filtrated, washed with ethyl acetate (40 mL) and unloaded from the filter. The crude material is then suspended in a mixture of ethyl acetate (200 mL) and ethanol (50 mL), heated to reflux and cooled to 0° C. Once cold, the suspension is stirred for 1 h at that temperature. The precipitate is then filtrated, washed with ethyl acetate (40 mL) and dried at 40° C. under vacuum (20 mbar) for 15 h affording a white-beige solid (19.4 g, 50%, 3-methylamino-1-thiophen-2-yl-propan-1-one mesylate according to $^1$H-NMR); $^1$H-NMR (DMSO-$d_6$, 400 MHz): 8.5 (2H, s, broad), 8.1 (1H, dm), 8.0 (1H, dm), 7.30 (1H, dd), 3.42 (2H, t), 3.3 (2H, s, broad), 2.6 (3H, s, broad), 2.38 (3H, s); $^{13}$C-NMR (DMSO-$d_6$, 100 MHz): 189.9, 142.6, 135.4, 133.9, 128.0, 43.2, 39.6, 34.5, 32.7.

GENERAL PROCEDURE FOR EXAMPLES 2 to 17

A mixture of the solvent, 1 equivalent (1 eq) of the methyl ketone of formula IV ($R^1$ specified in table 1), the primary alkyl amine of formula V and/or a salt thereof (1.1 to 2.0 eq), formaldehyde or a source thereof (1.1 to 1.5 eq), optionally additional sulfonic acid (total amount 1.0 to 1.1 eq), is heated in an autoclave at a total pressure above 1.5 bar for 1 h to 5 h. Afterwards, the reaction solution is cooled to room temperature (RT). Optionally the reaction solvent can than be removed partly or in whole and a solvent like ethyl acetate or isopropyl alcohol can be added under stirring, if necessary to facilitate precipitation of the product. The suspension is cooled (0 to 20° C.), filtered after precipitation (0.5 to 10 h), optionally washed and dried to afford a slightly white to light brown powder in a yield between 40 to 60%. The product can be recrystallized from ethyl acetate and/or an alcohol as specified above, preferably ethanol or isopropyl alcohol. The precipitate is then filtrated, washed with ethyl acetate and dried at about 40° C. under vacuum (about 20 mbar) for 15 h affording white-beige to light-brown solids.

To facilitate reaction series, with exception of example 11 and 17, all examples have been carried out in the presence of methanesulfonic acid (MSA) or using the respective alkyl-, aryl- or aralkylammonium methanesulfonate salt. In example 11 (+)-camphor-10-sulfonic acid ((+)—CSA) has been added to an ethanolic solution of methylamine. In example 17, methyl-ammonium p-toluenesulfonate has been used. Additionally, in examples 13 and 16 the respective amine and the sulfonic acid have been added separately and mixed within the reaction vessel. Examples 1 to 16 afforded total yields between 40 to 60%. The expected reaction products could be isolated in a ratio of about 2:1 compared to the respective starting amine. The starting amines of formula V remain unchanged and can be used for further reactions.

COMPARATIVE EXAMPLE 1 (C1)

A mixture of 2-butanol (40 mL), MAMS (16.5 g, 130 mmol), 2-acetylthiophene (11.0 g, 87.2 mmol) and paraformaldehyde (2.6 g, 86.6 mmol) is heated to 80° C. under atmospheric pressure. After 4 h at that temperature, the reaction mixture is cooled to 25° C. The reaction mixture is concentrated to dryness and a mixture of ethanol (20 mL) and ethyl acetate (400 mL) is added to the residue, then the resulting suspension is stirred for 30 minutes at 25° C. Afterwards, the precipitate is filtrated, washed with ethyl acetate (40 mL) and unloaded from the filter. The crude material is then suspended in a mixture of ethyl acetate (200 mL) and ethanol (50 mL), heated to reflux and cooled to 0° C. Once cold, the suspension is stirred for 1 h at that temperature, the precipitate is filtrated, washed with ethyl acetate (40 mL) and dried at 40° C. under vacuum (20 mbar) for 15 h affording a rosy solid. The compounds of formula II and III have been formed in poor yields (about 40% overall) in almost equal ratio. Data of 3,3'-(methylamino)bis[1-(thiophen-2-yl)propan-1-one]mesylate:
$^1$H-NMR (DMSO-$d_6$, 400 MHz): 9.4 (1H, s, broad), 8.1 (4H, m), 7.3 (2H, m), 3.4-3.6 (8H, m), 2.90 (3H, s), 2.38 (3H, s); $^{13}$C-NMR (DMSO-$d_6$, 100 MHz): 189.6, 142.7, 135.3, 134.0, 128.9, 50.3, 40.3, 39.6, 33.1.

COMPARATIVE EXAMPLE 2 (C2)

A mixture of isopropyl alcohol (30 mL), MAMS (5.6 g, 44 mmol), 2-acetylthiophene (10.1 g, 80 mmol), paraformaldehyde (3.2 g, 108 mmol) and MSA (about 0.1 g) is heated to reflux at 84° C. under normal pressure. After 20 h at that temperature, the precipitate is filtrated at about 80° C., washed with isopropyl alcohol (3×20 mL) and dried at 40° C. under vacuum (20 mbar) for 15 h affording a white solid. The compound of formula I could be isolated only in traces. The compound of formula III (3,3'-(methylamino)bis[1-(thiophen-2-yl)propan-1-one]mesylate) could be isolated in about 40% overall yield.

TABLE 1

Reaction conditions for examples 1 to C2

| No. | Ketone $R^1$ | Amine $R^2$ | Solvent | Temp [° C.] | Pressure [bar] | Time | Ketone [mmol] | Amine [mmol] | Acid [mmol] | $CH_2O$ [mmol] |
|---|---|---|---|---|---|---|---|---|---|---|
| 1 | thienyl | methyl | ethanol | 120 | 4.5 | 3 h | 87.2 | 130.0 | 130.0 | 86.6 |
| 2 | thienyl | methyl | ethanol | 120 | 4.5 | 1 h | 87.2 | 130.0 | 130.0 | 86.6 |
| 3 | thienyl | methyl | ethanol | 120 | 4.5 | 3 h | 87.2 | 130.0 | 130.0 | 131.0 |
| 4 | thienyl | methyl | ethanol | 120 | 4.5 | 3 h | 87.2 | 130.0 | 138.7 | 86.6 |
| 5 | thienyl | methyl | TFE | 120 | 4.8 | 4 h | 87.2 | 130.0 | 130.0 | 130.0 |
| 6 | thienyl | methyl | methanol | 115 | 5.8 | 4 h | 87.2 | 130.0 | 130.0 | 130.0 |
| 7 | thienyl | methyl | iso-PropOH | 120 | 4 | 4 h | 87.2 | 130.0 | 130.0 | 86.6 |

TABLE 1-continued

Reaction conditions for examples 1 to C2

| No. | Ketone $R^1$ | Amine $R^2$ | Solvent | Temp [° C.] | Pressure [bar] | Time | Ketone [mmol] | Amine [mmol] | Acid [mmol] | CH$_2$O [mmol] |
|---|---|---|---|---|---|---|---|---|---|---|
| 8  | thienyl | methyl | sec-BuOH    | 120   | 2.8     | 4 h  | 87.2  | 130.0 | 130.0 | 86.6  |
| 9  | thienyl | methyl | DME         | 120   | 3.2     | 3 h  | 87.2  | 130.0 | 130.0 | 86.6  |
| 10 | thienyl | methyl | 1,4-dioxane | 120   | n.a.    | 4 h  | 87.2  | 130.0 | 130.0 | 130.0 |
| 11 | thienyl | methyl | ethanol     | 120   | 4.5-4.8 | 4 h  | 174.0 | 259.0 | 260.0 | 173.0 |
| 12 | thienyl | ethyl  | ethanol     | 120   | 5       | 5 h  | 87.2  | 130.0 | 130.0 | 86.6  |
| 13 | thienyl | benzyl | ethanol     | 120   | 4.8     | 4 h  | 87.2  | 130.0 | 130.0 | 130.0 |
| 14 | phenyl  | ethyl  | ethanol     | 120   | 4.8     | 4 h  | 87.2  | 130.0 | 130.0 | 130.0 |
| 15 | phenyl  | methyl | ethanol     | 120   | 4.8     | 4 h  | 87.2  | 130.0 | 130.0 | 130.0 |
| 16 | phenyl  | benzyl | ethanol     | 120   | 4.8     | 4 h  | 87.2  | 130.0 | 130.0 | 130.0 |
| 17 | thienyl | methyl | ethanol     | 120   | n.a.    | 4 h  | 43.7  | 40.0  | 40.0  | 43.3  |
| C1 | thienyl | methyl | sec-BuOH    | 80    | 1       | 4 h  | 87.2  | 130.0 | 130.0 | 86.6  |
| C2 | thienyl | methyl | iso-PropOH  | reflux| 1       | 20 h | 80.0  | 44.0  | 44.0  | 44.9  | n.a. value not available
TFE = 2,2,2-trifluoroethanol, iso-PropOH = isopropyl alcohol, sec-BuOH = sec-butanol, DME = dimethyl ether.

NMR data of new compounds of examples 11 to 17 are given below:

EXAMPLE 11

3-Methylamino-1-thiophen-2-yl-propan-1-one 1-(S)-(7,7-dimethyl-2-oxobicyclo[2.2.1]hept-1-yl)methane Sulfonate $^1$H-NMR (DMSO-d$_6$, 400 MHz): 8.4 (2H, s, broad), 8.1 (1H, dm), 8.0 (1H, dm), 7.29 (1H, dd), 3.44 (2H, t), 3.27 (2H, t), 2.92 (1H, d), 2.64 (3H, s), 2.6 (1H, m), 2.43 (1H, d), 2.2 (1H, m), 2.0 (1H, m), 1.9 (1H, m), 1.80 (1H, d), 1.3 (2H, m), 1.04 (3H, s), 0.73 (3H, s).

EXAMPLE 12

3-Ethylamino-1-thiophen-2-yl-propan-1-one mesylate $^1$H-NMR (DMSO-d$_6$, 400 MHz): 8.4 (2H, s, broad), 8.1 (1H, dm), 8.0 (1H, dm), 7.3 (1H, m), 3.40 (2H, t), 3.3 (2H, s, broad), 3.0 (2H, s, broad), 2.32 (3H, s), 1.20 (3H, t).

EXAMPLE 13

3-Benzylamino-1-thiophen-2-yl-propan-1-one mesylate $^1$H-NMR (DMSO-d$_6$, 400 MHz): 8.8 (2H, s, broad), 8.1 (1H, dm), 8.0 (1H, dm), 7.5 (5H, m), 7.3 (1H, m), 4.23 (2H, s), 3.44 (2H, t), 3.30 (2H, t), 2.31 (3H, s).

EXAMPLE 14

3-Methylamino-1-phenyl-propan-1-one mesylate $^1$H-NMR (DMSO-d$_6$, 400 MHz): 8.0 (2H, dm), 7.7 (1H, tm), 7.6 (2H, tm), 7.5 (2H, s, broad), 3.47 (2H, t), 3.27 (2H, t), 2.64 (3H, s), 2.31 (3H, s).

EXAMPLE 15

3-Ethylamino-1-phenyl-propan-1-one mesylate $^1$H-NMR (DMSO-d$_6$, 400 MHz): 8.5 (2H, s, broad), 8.0 (2H, dm), 7.7 (1H, tm), 7.6 (2H, tm), 3.50 (2H, t), 3.3 (2H, s, broad), 3.0 (2H, s, broad), 2.38 (3H, s), 1.22 (3H, t).

EXAMPLE 16

3-Benzylamino-1-phenyl-propan-1-one mesylate $^1$H-NMR (DMSO-d$_6$, 400 MHz): 8.8 (2H, s, broad), 8.0 (2H, dm), 7.7 (1H, m), 7.3-7.6 (7H, m), 4.25 (2H, s), 3.50 (2H, t), 3.30 (2H, t), 2.31 (3H, s).

EXAMPLE 17

3-Methylamino-1-thiophen-2-yl-propan-1-one p-toluenesulfonate $^1$H-NMR (CDCl$_3$, 400 MHz): 8.8 (2H, s, broad), 7.7 (2H, dm), 7.6 (2H, m), 7.1 (2H, dm), 7.0 (1H, m), 3.5 (2H, m), 3.4 (2H, m), 2.75 (3H, m, symm), 2.30 (3H, s).

The compounds of formula III, obtained in comparative examples C1 and C2 can be cleaved in the presence of sulfonic acid and additional amine into the aminoketones of formula II. The added amine in comparative examples C3 to C6 was MAMS. 4 different solvents have been tried, diglyme, acetonitrile, methyl isobutyl ketone (MIBK) and N-methylpyrrolidone (NMP). Reactions have been carried out under pressure of about 4 to 5 bar. Yields of comparative examples C3 to C6 ($R^1$ and $R^2$ specified in table 2) are below 50%. In every case the product contained unidentified side-products.

TABLE 2

Cleavage of compounds of formula III

| No. | Ketone $R^1$ | Amine $R^2$ | Acid | Solvent | Temp [° C.] | Vessel | Time |
|---|---|---|---|---|---|---|---|
| C3 | thienyl | methyl | MSA | diglyme      | 120 | autoclave | 5.5 h |
| C4 | thienyl | methyl | MSA | acetonitrile | 120 | autoclave | 5.5 h |
| C5 | thienyl | methyl | MSA | MIBK         | 120 | autoclave | 5.5 h |
| C6 | thienyl | methyl | MSA | NMP          | 120 | autoclave | 5.5 h |

The salts of the aminoketones of formula II with sulfonic acids for asymmetrically hydrogenating in steb b) of the present processes are obtainable either with the Mannich reaction under pressure as outlined above in examples 1 to 17 accordingly to step a) or by mixture of a sulfonic acid and a free base of the β-aminoketones of formula II. The free bases of β-aminoketones of formula II can be obtained easily by hydrolyzing salts, such as the hydro-chlorides, in the presence of an aqueous base and subsequent extraction with an organic solvent. Examples 18 to 20 in table 3 illustrate a two step reaction starting with the hydrochlorides of said β-aminoketones obtainable according to WO-A 2004/005239, with $R^1$ and $R^2$ as specified in the table. Yield was at least 83%.

EXAMPLE 18

Preparation of 3-methylamino-1-thiophen-2-yl-propan-1-one mesylate from 3-methylamino-1-thiophen-2-yl-propan-1-one hydrochloride following the procedure of example 20, amounts and conditions as specified in table 2.

EXAMPLE 19

Preparation of 1-(S)-(7,7-dimethyl-2-oxobicyclo[2.2.1]hept-1-yl)methane sulfonate of 3-methylamino-1-thiophen-2-yl-propan-1-one from 3-methylamino-1-thiophen-2-yl-propan-1-one hydrochloride following the procedure of example 20, amounts and conditions as specified in table 2.

EXAMPLE 20

Preparation of 3-methylamino-1-thiophen-2-yl-propan-1-one p-toluenesulfonate from 3-methyl-amino-1-thiophen-2-yl-propan-1-one hydrochloride according to table 2. To a mixture of 3-methylamino-1-thiophen-2-yl-propan-1-one hydrochloride (29.2 g, 0.142 mol), methyl tert-butyl ether (MTBE) (510 mL) and water (60 mL) cooled to 5° C. is added within 15 minutes aqueous sodium hydroxide (38.4 g of a 20 wt % aqueous solution, 0.192 mol). At the end of the addition, the reaction mixture is stirred for 10 additional minutes at that temperature and the two phases are separated. The organic phase is washed with water (180 mL), then the collected aqueous phases are extracted with MTBE (2×150 mL). The collected organic phases are then cooled to 5° C. and once cold, a mixture of p-toluenesulfonic acid hydrate (25.8 g, 0.136 mol) and methanol (20 mL) is added dropwise in 15 minutes. The product crystallizes spontaneously during the addition. At the end of the addition, the reaction mixture is allowed to stand at 25° C. and stirred at that temperature for 30 minutes, then the precipitate is filtrated, washed with MTBE (50 mL) and dried at 50° C. under vacuum (20 mbar) for 15 h affording a light brown-rosy solid (39.5 g, 85%, relative pure product, according to $^1$H-NMR). If necessary, the crude product can be recrystallised from isopropyl alcohol (150 mL) affording a light rosy solid (32.7 g, 70%), pure product).

(0.05 to 0.5 eq), methanol (40 to 50 mL) and water (10 to 12.5 mL) is charged under nitrogen in an autoclave. The autoclave is then closed, purged several times with nitrogen, and then hydrogen is added until the pressure reaches 10 (examples 24 and 25) or 30 bars at 25° C. After the time as indicated in table 4 h at the respective temperature under stirring, the remaining hydrogen is released carefully, then the reaction mixture is diluted to about 100 mL using a 4:1 (vol:vol) mixture of methanol and water. Once cold, it is transferred into a 50 mL round bottom flask and concentrated to dryness affording the product as salts of a sulfonic acid. The amount of the starting aminoketones referenced in table 4 corresponds to the amount of the sulfonic acid of the respective amino ketone. The $2^{nd}$ column of table 4 denotes the example from which the respective starting β-aminoketone sulfonate has been taken.

In the examples 21, 22, 23, 24 and 26 the β-aminoalcohols of formula Ia have been isolated as the free base by treatment of the residue after concentrating with a mixture of MTBE (10 mL) and aqueous sodium hydroxide (5 mL of a 20% aqueous solution). The two phases are then separated and the aqueous phase is extracted with MTBE (2×5 mL). Afterwards, the collected organic phases (in which a fine precipitate is contained) are dried over sodium sulfate, filtrated and concentrated to dryness affording a brown oil which normally crystallises after a few hours. The release of the free bases of the aminoalcohols of formula I from the sulfonates corresponds to the procedure outlined in examples 18 to 20.

GENERAL PROCEDURE FOR COMPARATIVE EXAMPLES C12 to C16

A mixture of the salt of the β-aminoketone of formula II (1 eq), as indicated in table 4, in methanol (25 mL) is charged under nitrogen in an autoclave. Afterwards, a solution of the catalyst in methanol (10 mL) prepared under nitrogen is added via a syringe to the first mixture. The autoclave is then closed and purged several times with nitrogen, then hydrogen is added until the pressure reaches 30 bars and the mixture is heated up to the temperature indicated in table 4. After the respective time at that temperature under stirring, the reaction mixture is cooled to 25° C. Once cold, it is transferred into a 50 mL round bottom flask and concentrated to dryness affording the product as salt of a sulfonic acid.

TABLE 3

Preparation of salts by anion exchange

| No. | Temp [° C.] | Ketone $R^1$ | Amine $R^2$ | Acid | Base | Solvent | Temp [° C.] | Time |
|---|---|---|---|---|---|---|---|---|
| 18 | $1^{st}$ step | thienyl | methyl | — | NaOH | H$_2$O/MTBE | 5 | 50 min |
|  | $2^{nd}$ step | — | — | MSA |  | MeOH | 0 | 1.5 h |
| 19 | $1^{st}$ step | thienyl | methyl | — | NaOH | H$_2$O/MTBE | 5 | 20 min |
|  | $2^{nd}$ step | — | — | (+)-CSA. |  | MeOH | 0 | 53 min |
| 20 | $1^{st}$ step | thienyl | methyl | — | NaOH | H$_2$O/MTBE | 5 | 25 min |
|  | $2^{nd}$ step | — | — | tosylic acid |  | MeOH | 0 | 45 min |

The hydrogenation of β-aminoketone sulfonates of formula II is outlined in examples 21 to C16 below.

GENERAL PROCEDURE FOR EXAMPLES 21 to 26

A mixture of the catalyst as indicated in table 4, a β-aminoketone sulfonate of formula II (1 eq), potassium carbonate

EXAMPLE 25

Data of (S)-3-methylamino-1-thiophen-2-yl-propan-1-ol mesylate of table 4 mp (uncorrected): 62-65° C.; $^1$H-NMR (DMSO-d$_6$, 400 MHz): 8.4 (2H, s, broad), 7.4 (1H, dm), 7.0 (2H, m), 6.0 (1H, s, broad), 4.94 (1H, m, symm.), 3.00 (2H, m, symm.), 2.59 (3H, s), 2.39 (3H, s), 2.0 (2H, m).

TABLE 4

Asymmetric hydrogenation of sulfonates of compounds of formula II

| No. | Starting ketone | Ketone [mmol] | Catalyst | Catalyst [μmol] | Temp [° C.] | Time | S/C | Conversion | ee |
|---|---|---|---|---|---|---|---|---|---|
| 21 | example 17 | 1.05 | DUAN | 5.12 | 50 | 5 h | 205 | 100% | 86% |
| 22 | example 17 | 1.05 | DUAN | 5.12 | 25 | 5 h | 205 | 100% | 94% |
| 23 | example 11 | 1.20 | DUAN | 11.0 | 25 | 5 h | 109 | 100% | 94% |
| 24 | example 5 | 27.10 | DUAN | 3.6 | 25 | 41 h | 7511 | 100% | 98% |
| 25 | example 5 | 43.80 | DUAN | 4.4 | 40 | 21 h | 10029 | 100% | 92% |
| 26 | example 5 | 1.20 | DUAN | 11.0 | 25 | 5 h | 109 | 100% | 94% |
| C7 | example 17 | 0.45 | TANG | 5.3 | 55 | 5 h | 85 | 15% | 80% |
| C8 | example 17 | 0.45 | DUPH | 4.5 | 55 | 5 h | 100 | 15% | 99% |
| C9 | example 17 | 2.11 | DUAN | 10.0 | 50 | 18 h | 211 | 40% | 87% |
| C10 | example 11 | 1.20 | DUPH | 11.0 | 50 | 5 h | 109 | 20% | 95% |
| C11 | example 11 | 1.20 | DUAN | 11.0 | 50 | 5 h | 109 | 20% | 87% |
| C12 | example 5 | 1.20 | TANG | 11.0 | 80 | 5 h | 109 | 50% | 79% |
| C13 | example 5 | 1.20 | DUPH | 11.0 | 50 | 5 h | 109 | 15% | 91% |
| C14 | example 5 | 1.20 | DUPH | 11.0 | 80 | 4.5 h | 109 | 20% | 88% |
| C15 | example 5 | 1.20 | DUAN | 11.0 | 50 | 5 h | 109 | 35% | 88% |
| C16 | example 5 | 1.20 | DUAN | 11.0 | 80 | 5 h | 109 | 40% | 79% |

Diphosphine ligands, commercially available e.g. from Chiral Quest, Inc, Monmouth Junction, N.J., USA, used in the examples 21 to C16 are: [Rh((R,R,S,S)-Tangphos)(norbornadiene)]$BF_4$=TANG, [(S,S)-Me-Duphos-Rh]$BF_4$=DUPH, [Rh(NBD)($R_P$,$R_P$,$S_C$,$S_C$-DuanPhos)]$BF_4$=DUAN.

EXAMPLE 27

(S)-3-methylamino-1-thiophen-2-yl-propan-1-ol p-toluenesulfonate

A mixture of (S)-3-methylamino-1-thiophen-2-yl-propan-1-ol (5.0 g, 29.2 mmol), methylene chloride (50 mL), p-toluenesulfonic acid hydrate (5.55 g, 29.2 mmol) and methanol (20 mL) is stirred 1 h at 25° C., then concentrated to dryness. The residue (10.8 g) which solidifies after a few hours is finally recrystallised from butanol (30 mL) affording a white powder (6.0 g, 60%); $^1$H-NMR (DMSO-$d_6$, 400 MHz): 8.1 (1H, s, broad), 7.5 (2H, dm), 7.42 (1H, dd), 7.1 (2H, dm), 7.0 (2H, m), 4.92 (1H, dd), 2.97 (2H, m, symm.), 2.57 (3H, s), 2.28 (3H, s), 2.0 (2H, m); $^{13}$C-NMR (DMSO-$d_6$, 100 MHz): 149.3, 145.5, 137.6, 128.0, 126.6, 125.4, 124.4, 123.0, 66.1, 45.8, 35.1, 32.7, 20.7.

EXAMPLE 28

(S)-3-methylamino-1-thiophen-2-yl-propan-1-ol 1-(S)-(7,7-dimethyl-2-oxobicyclo[2.2.1]hept-1-yl)-methane Sulfonate A mixture of (S)-3-methylamino-1-thiophen-2-yl-propan-1-ol (34.2 g, 200 mmol) and ethyl acetate (400 mL) is heated to 30° C., then a mixture of (+)-camphor-10-sulfonic acid (46.4 g, 200 mmol), ethyl acetate (100 mL) and ethanol (100 mL) is added dropwise at 30° C. in 40 minutes. At the end of the addition, the resulting solution is heated to 50° C., stirred for 15 minutes at that temperature, then cooled to 25° C. Once cold, the reaction mixture is concentrated to dryness and ethyl acetate (500 mL) is added to the residue. The resulting mixture is then heated to reflux, kept at that temperature for 15 minutes, then cooled to 25° C. in 30 minutes while seeding the reaction mixture when the temperature reaches about 40° C. Once cold, the resulting suspension is stirred for 30 additional minutes. Afterwards, the precipitate is filtrated, washed with ethyl acetate (2×50 mL) and dried at 40° C. under vacuum (20 mbar) for 15 h affording a white solid (71.5 g, 89%); $^1$H-NMR (CDCl$_3$, 400 MHz): 7.2 (1H, dm), 7.0 (1H, m), 6.9 (1H, m), 5.21 (1H, t), 3.3 (3H, m), 2.82 (1H, d), 2.75 (3H, s), 2.50 (1H, m, symm.), 2.3 (3H, m), 2.1 (1H, m), 2.0 (1H, m), 1.85 (1H, d), 1.74 (1H, m, symm.), 1.4 (1H, m), 1.04 (3H, s), 0.82 (3H, s).

The invention claimed is:

1. A process for the preparation of N-monosubstituted β-aminoalcohol sulfonates of formula

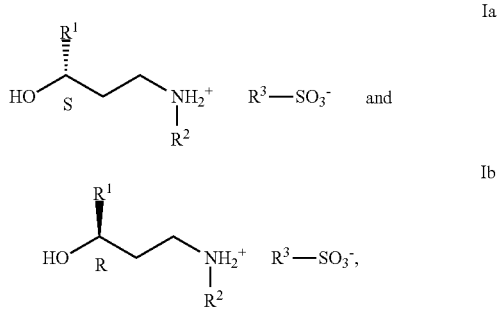

wherein $R^1$ is $C_{6-20}$ aryl or $C_{4-12}$ heteroaryl, each optionally being substituted with one or more halogen atoms and/or one or more $C_{1-4}$ alkyl or $C_{1-4}$ alkoxy groups, $R^2$ is selected from the group consisting of $C_{1-4}$ alkyl, $C_{3-8}$ cycloalkyl and $C_{6-20}$ aryl, each aryl optionally being substituted with one or more halogen atoms and/or one or more $C_{1-4}$ alkyl or $C_{1-4}$ alkoxy groups, and wherein $R^3$ is selected from the group consisting of $C_{1-18}$ alkyl, $C_{6-20}$ cycloalkyl, $C_{6-20}$ aryl and $C_{7-20}$ aralkyl residues, comprising the steps of
a) reacting a mixture comprising
  (i) a methyl ketone of formula

    IV wherein R¹ is as defined above,
(ii) a primary amine of formula

    V, wherein R² is as defined above, and
(iii) formaldehyde or a source of formaldehyde selected from the group consisting of formaldehyde in aqueous solution, 1,3,5-trioxane, paraformaldehyde and mixtures thereof,
in the presence of a sulfonic acid of the formula

    VI wherein R³ is as defined above,
optionally in an organic solvent, said organic solvent optionally containing water, to afford a β-aminoketone sulfonate of formula

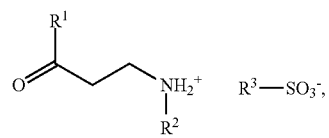    II wherein R, R² and R³ are as defined above,
and
b) asymmetrically hydrogenating said sulfonate, to afford a β-aminoalcohol sulfonate of formula I, wherein R¹, R² and R³ are as defined above, in the presence of a base and a catalyst, the catalyst comprising a transition metal and a diphosphine ligand, at a hydrogen pressure of 5 to 50 bar, in a polar solvent, optionally in the presence of water.

2. A process for the preparation of N-monosubstituted β-aminoalcohol sulfonates of formula

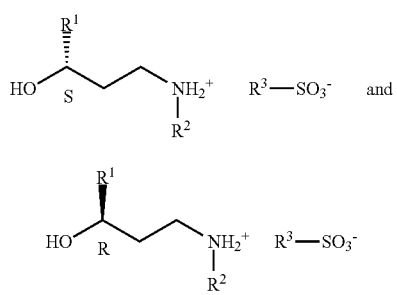

Ia and

Ib wherein R¹ is C$_{6-20}$ aryl or C$_{4-12}$ heteroaryl, each optionally being substituted with one or more halogen atoms and/or one or more Ci$_{-4}$ alkyl or C$_{1-4}$ alkoxy groups, R² is selected from the group consisting of C$_{1-4}$ alkyl, C$_{3-8}$ cycloalkyl and C$_{6-20}$ aryl, each aryl optionally being substituted with one or more halogen atoms and/or one or more C$_{1-4}$ alkyl or C$_{1-4}$ alkoxy groups, and wherein R³ is selected from the group consisting of Ci$_{-18}$ alkyl, C$_{6-20}$ cycloalkyl, C$_{6-20}$ aryl and C$_{7-20}$ aralkyl residues, comprising asymmetrically hydrogenating a β-aminoketone sulfonate of formula

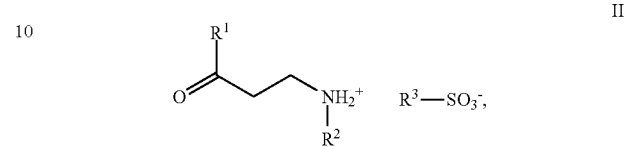    II wherein R, R and R are as defined above,
in the presence of a base and a catalyst, the catalyst comprising a transition metal and a diphosphine ligand, at a hydrogen pressure of 5 to 50 bar, in a polar solvent, optionally in 1 o the presence of water.

3. The process of claim 1, wherein R¹ is 2-thienyl, optionally being substituted with one or more halogen atoms, and R² is selected from the group consisting of methyl, ethyl, tert-butyl and cyclopropyl.

4. The process of claim 1, wherein the β-aminoalcohol of formula I is selected from the group consisting of (<S)-(-)-3-iV-methylamino-1-(2-thienyl)-1-propanol, (,S)-(-)-3-7V-methyl-amino-1-(3-chloro-2-thienyl)-1-propanol, (i?)-(+)-3-iV-methylamino-1-(2-thienyl)-1-propanol and (i?)-(+)-3-N-methylamino-1-(3-chloro-2-thienyl)-20 1-propanol.

5. The process of claim 1, wherein R³ of the sulfonic acids of the formula VI is selected from the group consisting of
  i) linear or branched alkyl residues, consisting of 1 to 18 carbon atoms, containing one 15 or more substituents of the group consisting of amino, halogen and hydroxy,
  ii) cycloalkyl residues, consisting of 6 to 20 carbon atoms, optionally containing one or more nitrogen or oxygen atoms and/or one or more substituents of the group consisting of amino, halogen and hydroxy, and
  iii) mono- or polycyclic aromatic or araliphatic residues, consisting of 6 to 20 carbon so atoms, optionally containing one or more nitrogen or oxygen atoms and/or one or more substituents of the group consisting of amino, halogen and hydroxy.

6. The process of claim 1, wherein the base, is a metal carbonate.

7. The process of claim 1, wherein the transition metal is selected from the group consisting of rhodium, ruthenium or indium, preferably rhodium.

8. The process of claim 1, wherein the diphosphine ligand is selected from the group consisting of

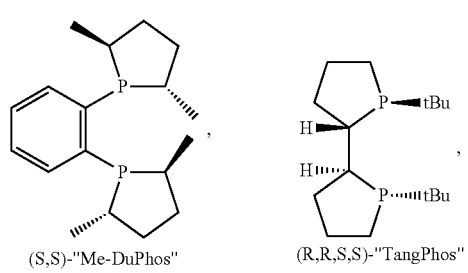

(S,S)-"Me-DuPhos"    (R,R,S,S)-"TangPhos"

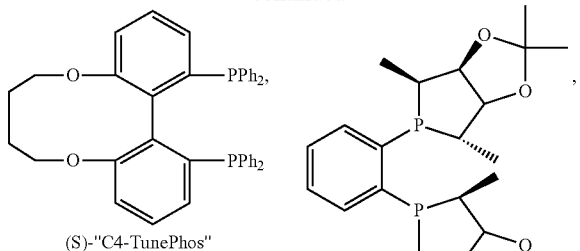

(S)-"C4-TunePhos"

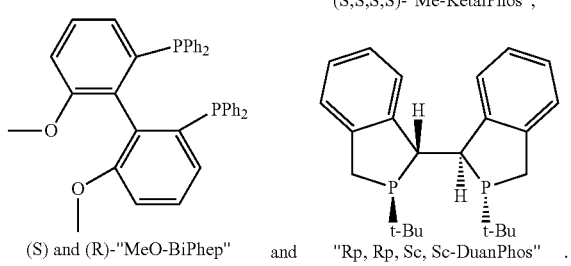

(S,S,S,S)-"Me-KetalPhos",

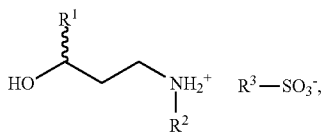

(S) and (R)-"MeO-BiPhep"    and    "Rp, Rp, Sc, Sc-DuanPhos"

9. β-Aminoalcohol sulfonates of the formula $$\underset{R^2}{\overset{R^1}{HO}}\diagdown\diagup\diagdown\diagup NH_2^+ \quad R^3-SO_3^-, \qquad I$$

wherein $R^1$ is $C_{6-20}$ aryl or $C_{4-12}$ heteroaryl, each optionally being substituted with one or more halogen atoms and/or one or more $C_{1-4}$-alkyl or $C_{1-4}$-alkoxy groups, $R^2$ is $C_{1-4}$-alkyl or $C_{6-20}$ aryl, each aryl optionally being substituted with one or more halogen atoms and/or one or more $C_{1-4}$ alkyl or $C_{1-4}$ alkoxy groups, and wherein $R^3$ is selected from the group consisting of $C_{1-18}$ alkyl, $C_{6-20}$ cycloalkyl, $C_{6-20}$ aryl and $C_{7-20}$ aralkyl residues.

10. The process of claim 2, wherein R.sup.1 is 2-thienyl, optionally being substituted with one or more halogen atoms, and R.sup.2 is selected from the group consisting of methyl, ethyl, tert-butyl and cyclopropyl.

11. The process of claim 2, wherein the .beta.-aminoalcohol of formula I is selected from the group consisting of (S)-(−)-3-N-methylamino-1-(2-thienyl)-1-propanol, (S)-(−)-3-N-methyl-amino-1-(3-chloro-2-thienyl)-1-propanol, (R)-(+)-3-N-methylamino-1-(2-thienyl)-1-propanol and (R)-(+)-3-N-methylamino-1-(3-chloro-2-thienyl)-1-propanol.

12. The process of claim 3, wherein the .beta.-aminoalcohol of formula I is selected from the group consisting of (S)-(−)-3-N-methylamino-1-(2-thienyl)-1-propanol, (S)-(−)-3-N-methyl-amino-1-(3-chloro-2-thienyl)-1-propanol, (R)-(+)-3-N-methylamino-1-(2-thienyl)-1-propanol and (R)-(+)-3-N-methylamino-1-(3-chloro-2-thienyl)-1-propanol.

13. The process of claim 10, wherein the .beta.-aminoalcohol of formula I is selected from the group consisting of (S)-(−)-3-N-methylamino-1-(2-thienyl)-1-propanol, (S)-(−)-3-N-methyl-amino-1-(3-chloro-2-thienyl)-1-propanol, (R)-(+)-(3)-N-methylamino-1-(2-thienyl)-1-propanol and (R)-(+)-3-N-methylamino-1-(3-chloro-2-thienyl)-1-propanol.

14. The process of claim 2, wherein R.sup.3 of the sulfonic acids of the formula VI is selected from the group consisting of
   i) linear or branched alkyl residues, consisting of 1 to 18 carbon atoms, containing one or more substituents of the group consisting of amino, halogen and hydroxyl,
   ii) cycloalkyl residues, consisting of 6 to 20 carbon atoms, optionally containing one or more nitrogen or oxygen atoms and/or one or more substituents of the group consisting of amino, halogen and hydroxyl, and
   iii) mono- or polycyclic aromatic or araliphatic residues, consisting of 6 to 20 carbon atoms, optionally containing one or more nitrogen or oxygen atoms and/or one or more substituents of the group consisting of amino, halogen and hydroxyl.

15. The process of claim 12, wherein R.sup.3 of the sulfonic acids of the formula VI is selected from the group consisting of
   i) linear or branched alkyl residues, consisting of 1 to 18 carbon atoms, containing one or more substituents of the group consisting of amino, halogen and hydroxyl,
   ii) cycloalkyl residues, consisting of 6 to 20 carbon atoms, optionally containing one or more nitrogen or oxygen atoms and/or one or more substituents of the group consisting of amino, halogen and hydroxyl, and
   iii) mono- or polycyclic aromatic or araliphatic residues, consisting of 6 to 20 carbon atoms, optionally containing one or more nitrogen or oxygen atoms and/or one or more substituents of the group consisting of amino, halogen and hydroxyl.

16. The process of claim 13, wherein R.sup.3 of the sulfonic acids of the formula VI is selected from the group consisting of
   i) linear or branched alkyl residues, consisting of 1 to 18 carbon atoms, containing one or more substituents of the group consisting of amino, halogen and hydroxyl,
   ii) cycloalkyl residues, consisting of 6 to 20 carbon atoms, optionally containing one or more nitrogen or oxygen atoms and/or one or more substituents, of the group consisting of amino, halogen and hydroxyl, and
   iii) mono- or polycyclic aromatic or araliphatic residues, consisting of 6 to 20 carbon atoms, optionally containing one or more nitrogen or oxygen atoms and/or one or more substituents of the group consisting of amino, halogen and hydroxyl.

17. The process of claim 2, wherein the base is a metal carbonate.

18. The process of claim 15, wherein the base is a metal carbonate.

19. The process of claim 16, wherein the base is a metal carbonate.

20. The process of claim 2, wherein the transition metal is selected from the group consisting of rhodium, ruthenium or iridium, preferably rhodium.

21. The process of claim 18, wherein the transition metal is selected from the group consisting of rhodium, ruthenium or iridium, preferably rhodium.

22. The process of claim 19, wherein the transition metal is selected from the group consisting of rhodium, ruthenium or iridium, preferably rhodium.

23. The process of claim 2, wherein the diphosphine ligand is selected from the group consisting of

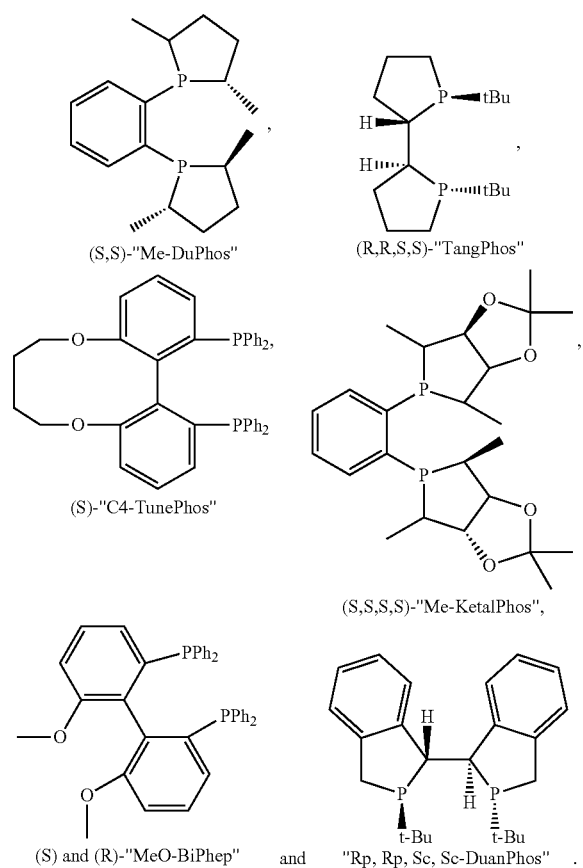
24. The process of claim 21, wherein the diphosphine ligand is selected from the group consisting of
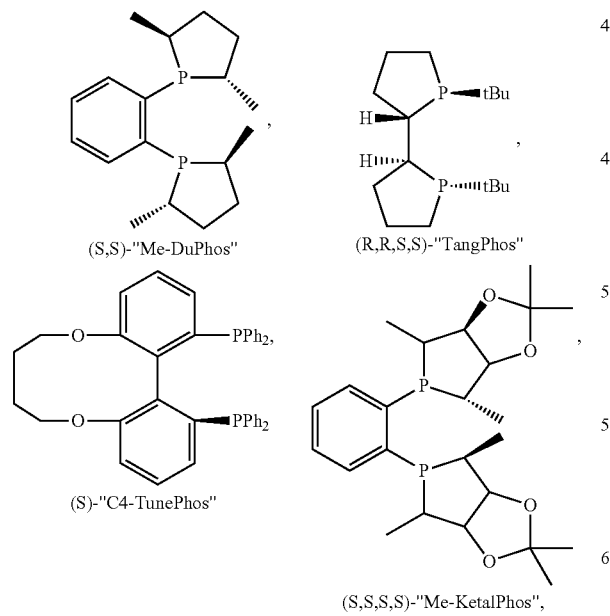
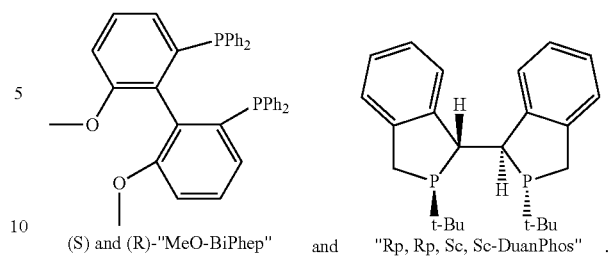
25. The process of claim 22, wherein the diphosphine ligand is selected from the group consisting of
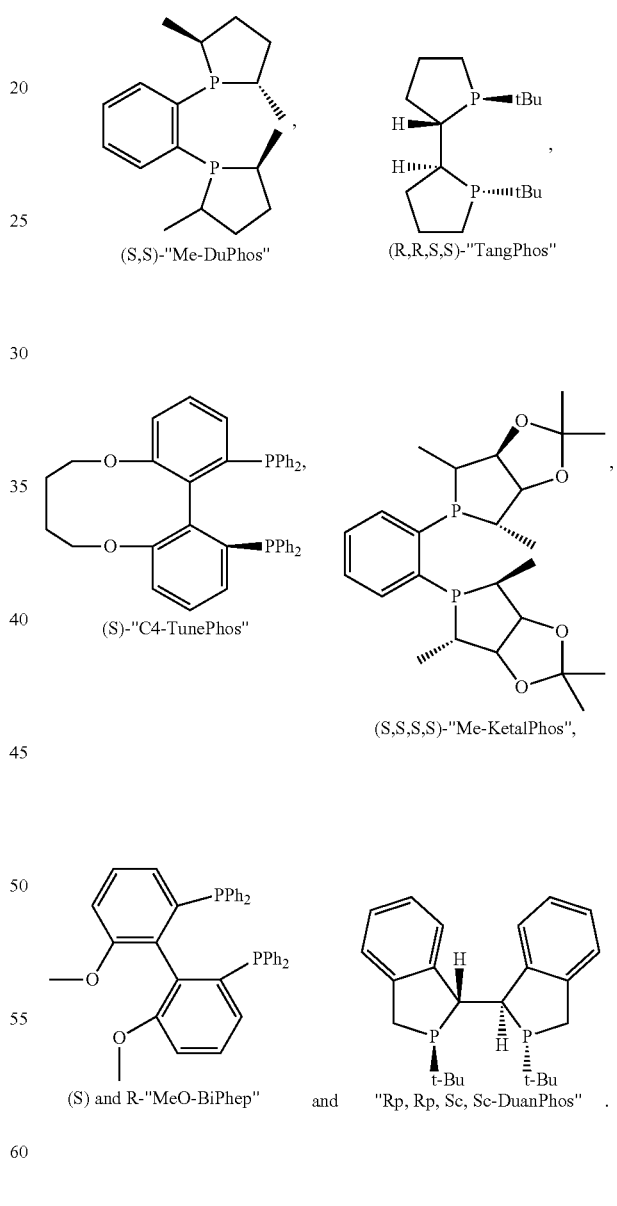
* * * * *

UNITED STATES PATENT AND TRADEMARK OFFICE
CERTIFICATE OF CORRECTION

PATENT NO. : 8,258,338 B2
APPLICATION NO. : 11/884542
DATED : September 4, 2012
INVENTOR(S) : Brieden et al.

It is certified that error appears in the above-identified patent and that said Letters Patent is hereby corrected as shown below:

IN THE SPECIFICATION

Column 3, line 28        Now reads:      "afforded (S)-3-chloro"
                         Should read:    -- afforded (s)-3-chloro --

Column 7, line 44        Now reads:      "7,7-dimethyl-2-oxobi-cyclo[2.2.1]hept-1-yl)"
                         Should read:    -- (7,7-dimethyl-2-oxobi-cyclo[2.2.1]hept-1-yl) --

Column 8, line 30        Now reads:      "2,3-butane-diol"
                         Should read:    -- 2,3-butanediol --

Column 8, line 35        Now reads:      "tri-ethylene"
                         Should read:    -- triethylene --

Column 8, line 61        Now reads:      "150°C.,"
                         Should read:    -- 150°C, --

Column 9, line 11        Now reads:      "50 to 80° C."
                         Should read:    -- 50 to 80°C --

Column 14, line 65       Now reads:      "1 to 17 and 21 to 26 no respectively"
                         Should read:    -- 1 to 17 and 21 to 26 respectively --

Column 17, line 27       Now reads:      "methane Sulfonate"
                         Should read:    -- methane sulfonate --

Column 18, line 59       Now reads:      "hydrogenating in steb b)"
                         Should read:    -- hydrogenating in step b) --

Signed and Sealed this
Fourth Day of December, 2012

David J. Kappos
*Director of the United States Patent and Trademark Office*

CERTIFICATE OF CORRECTION (continued)
U.S. Pat. No. 8,258,338 B2

| | | |
|---|---|---|
| Column 20, lines 5-6 | Now reads: | "as indicated in table 4 h" |
| | Should read: | -- as indicated in table 4 -- |
| | | |
| Column 21, line 56 | Now reads: | "methane Sulfonate" |
| | Should read: | -- methane sulfonate -- |
| | | |
| Column 22, line 66 | Now reads: | "$C_{6-2}O$ aryl" |
| | Should read: | -- $C_{6-20}$ aryl -- |
| | | |
| Column 23, line 65 | Now reads: | "$Ci_4$ alkyl" |
| | Should read: | -- $C_{1-4}$ alkyl -- |
| | | |
| Column 24, line 3 | Now reads: | "$Ci_{18}$ alkyl" |
| | Should read: | -- $C_{1-18}$ alkyl -- |
| | | |
| Column 24, lines 20-21 | Now reads: | "optionally in 1 o the presence of water" |
| | Should read: | -- optionally in the presence of water -- |

IN THE CLAIMS

| | | |
|---|---|---|
| Column 24, lines 26-31 (Claim 4) | Now reads: | "The process of claim 1, wherein the β-aminoalcohol of formula I is selected from the group consisting of (<S)-(— )-3-iV-methylamino-1-(2-thienyl)-1-propanol, (,S)-(-)-3-7V-methyl-amino-1-(3-chloro-2-thienyl)-1-propanol, (i?)-(+)-3-iVmethylamino-1 -(2-thienyl)- 1 -propanol and (i?)-(+)-3 -N-methylamino- 1 -(3 -chloro-2-thienyl)- 20 1 -propanol." |
| | Should read: | -- The process of claim 1, wherein the β-aminoalcohol of formula I is selected from the group consisting of (S)-(–)-3-N-methylamino-1-(2-thienyl)-1-propanol, (S)-(–)-3-N-methylamino-1-(3-chloro-2-thienyl)-1-propanol, (R)-(+)-3-N-methylamino-1-(2-thienyl)-1-propanol and (R)-(+)-3-N-methylamino-1-(3-chloro-2-thienyl)-1-propanol. -- |
| | | |
| Column 24, line 36 (Claim 5) | Now reads: | "containing one 15 or more substituents" |
| | Should read: | -- containing one or more substituents -- |
| | | |
| Column 24, line 43 (Claim 5) | Now reads: | "6 to 20 carbon so atoms" |
| | Should read: | -- 6 to 20 carbon atoms -- |
| | | |
| Column 24, line 52 (Claim 7) | Now reads: | "indium" |
| | Should read: | -- iridium -- |

CERTIFICATE OF CORRECTION (continued)
U.S. Pat. No. 8,258,338 B2

| Column 27, line 34 (Claim 23) | Now reads: | " (S) and R-"MeO-BiPhep " |
|---|---|---|
| | Should read: | -- (S) and R-"Me0-BiPhep -- |

| Column 28, line 11 (Claim 24) | Now reads: | " (S) and (R)-"MeO-BiPhep " |
|---|---|---|
| | Should read: | -- (S) and R-"Me0-BiPhep -- |